United States Patent [19]
Webb et al.

[11] Patent Number: 5,608,382
[45] Date of Patent: Mar. 4, 1997

[54] INFANT IDENTIFICATION AND SECURITY APPARATUS

[76] Inventors: Nicholas J. Webb, 5370 Basel Dr., Box 831, Wrightwood, Calif. 92397; James E. Ramsey, 23111 Marvilla La., Coto de Caza, Calif. 92679

[21] Appl. No.: 515,856

[22] Filed: Aug. 16, 1995

[51] Int. Cl.$^6$ ................................................. G08B 23/00
[52] U.S. Cl. ..................... 340/573; 340/825.34; 606/120
[58] Field of Search ............................... 340/573, 825.34, 340/825.32, 825.31; 235/380, 382; 606/120

[56] References Cited

U.S. PATENT DOCUMENTS

| | | | |
|---|---|---|---|
| 2,434,831 | 1/1948 | Brandenburg | 606/120 |
| 3,204,636 | 9/1965 | Kariher et al. | 606/120 |
| 3,854,482 | 12/1974 | Laugherty et al. | 606/120 |
| 4,709,136 | 11/1987 | Watanabe | 235/380 X |
| 4,857,716 | 8/1989 | Gombrich et al. | 340/825.34 X |
| 4,899,134 | 2/1990 | Wheeless, Jr. | 340/573 |
| 5,006,830 | 4/1991 | Merritt | 340/573 |
| 5,281,228 | 1/1994 | Wolfson | 606/120 |
| 5,440,295 | 8/1995 | Ciecwisz et al. | 340/573 |
| 5,512,879 | 4/1996 | Stokes | 340/573 |

OTHER PUBLICATIONS

Precision Dynamics Corp. brochure for SnugFit Mother/Infant Identification Wristbands, two pages, dated 1994.

*Primary Examiner*—Thomas Mullen
*Attorney, Agent, or Firm*—Jack Lo

[57] ABSTRACT

An infant identification and security system includes an umbilical cord clamp for being attached to the umbilical cord of an infant, a wristband for being worn on the infant's mother, a pair of information storage modules attached to the clamp and wristband, and a compatible terminal for reading and writing information to the storage modules. The modules contain distinctive identification information that is readable only by the terminal, and only after a predetermined password is entered into the terminal. A person wishing to carry the infant from a maternity ward is given permission to do so only after the identification information in her module is checked by hospital personnel for correspondence with the information in the infant's module. A pair of triggering elements are attached to the umbilical cord clamp for triggering a compatible alarm system when the infant is taken from the maternity ward.

16 Claims, 3 Drawing Sheets

INFANT IDENTIFICATION AND SECURITY APPARATUS

BACKGROUND OF THE INVENTION

1. Field of the Invention

This invention relates generally to anti-theft systems, specifically to an infant identification and security apparatus for identifying infants and preventing infant abductions in healthcare institutions.

2. Prior Art

Immediately after the birth of an infant, a small clamp is typically attached to the base of its umbilical cord to close it off, and the excess cord is cut off above the clamp. The remaining umbilical cord dries and falls off, along with the clamp, in about two weeks to leave a depression or navel on the infant's abdomen.

A variety of umbilical cord clamps have been offered. U.S. Pat. No. 3,204,636 to Kariher et al. (1965) shows an umbilical cord clamp with a pair of arms connected by a flexible hinge portion. An enlarged grip portion is arranged at the distal end of each arm. An extension with an oval hole is attached to one grip, and a L-shaped projection with an oval button at a distal end thereof is attached to the other grip. The oval button is radially offset with respect to the oval hole. When the arms are pressed together, the button is forced through the oval hole to lock the arms in a closed position. However, closing the clamp may be difficult, because the grips are positioned inwardly of the extension and projection, so that the required force is relatively high.

U.S. Pat. No. 3,854,482 to Laugherty et al. (1974) shows a clamp with hingeably connected arms, and grip portions arranged at the distal ends of the arms. A pair of flexible hooks extend inwardly from one grip for lockably mating with an open socket arranged on one side of the other grip. The hooks remain exposed after they are snapped into the open socket. Other umbilical cord clamps have been provided with security devices to combat infant abductions in healthcare institutions. U.S. Pat. No. 4,899,134 to Wheeless, Jr. (1990) shows a security umbilical cord clamp comprising a spring loop with a pair of handles extending from the ends thereof. A hidden triggering element is embedded within the loop for triggering a magnetic field alarm system, which typically includes a detection gate having twin vertical panels installed at a doorway. When the clamp and the attached infant are taken through the gate, the alarm is triggered. However, the Wheeless, Jr. clamp includes no locking mechanism, so that it can be easily defeated by simply removing it from the infant.

U.S. Pat. No. 5,006,830 to Merritt (1991) shows a security umbilical cord clamp with a pair of hinged arms, and grip portions arranged at the distal ends of the arms. The grip portions have inwardly pointing hooks arranged at their distal ends that interlock when the arms are pressed together around the umbilical cord of an infant. A triggering element is completely embedded within one arm for triggering an alarm system if the clamp is carried from a protected area. One arm is provided with a distinctive identification mark, which can be a serial number, bar code, color code, or letter combination. A bracelet with a corresponding distinctive identification mark is worn on a person authorized to carry the infant from the protected area, such as the infant's mother. Before anyone can carry the infant from the protected area, the mark on the person's bracelet is checked for correspondence with the mark on the infant's clamp. However, the information in a bar code can be read by unaided eyes, because a bar code typically includes a series of stripes and a corresponding numeric code, so that if the stripes cannot be read by a reader, the numeric code can be manually read by an operator and entered into the reader via a keypad. Therefore, in any embodiment, the mark is visible identification information that can be easily read with unaided eyes, so that a resourceful abductor can forge a matching bracelet. An abductor can also defeat the alarm system by prying the hooks apart and removing the clamp.

U.S. Pat. No. 5,281,228 to Wolfson (1994) shows an umbilical cord clamp with a pair of hinged arms, and a label affixed to one of the arms. A hook extending inwardly from one arm is arranged to interlock with a hole on the other arm. However, the Wolfson device offers no capability for triggering an alarm system, or a matching bracelet for the mother, so that it provides little security.

Although the Kariher and Laugherty clamps can each incorporate a security device, the Kariher clamp can be removed from the infant by simply prying the L-shape projection away from the extension, and the Laugherty clamp can be easily removed by pinching the hooks together to release them from the socket.

OBJECTS OF THE INVENTION

Accordingly the primary object of the present invention is to provide an infant identification and security apparatus that positively matches an infant to its mother.

Another object of the present invention is to provide an infant identification and security apparatus that is provided with distinctive identification information not readable to an unaided eye for security.

Another object of the present invention is to provide an infant identification and security apparatus that is provided with distinctive identification information readable only to a person with knowledge of a predetermined password.

Yet another object of the present invention is to provide an infant identification and security apparatus that triggers an alarm system when the infant is taken from a predetermined area.

Still another object of the present invention is to provide an infant identification and security apparatus that cannot be easily defeated by an unauthorized person.

Still another object of the present invention is to provide an infant identification and security apparatus that is provided with an umbilical cord clamp that is removable by an authorized person with a clamp cutting tool in an emergency.

Other objects of the invention will become apparent from a study of the following description and the accompanying drawings.

SUMMARY OF THE INVENTION

An infant identification and security apparatus includes an umbilical cord clamp with a pair of hingeably connected arms, and a grip portion arranged at the distal end of each arm. A projection extending inwardly from one grip is arranged to interlock with a hole on the other grip. An information storage module with distinctive identification information stored therein is attached to the clamp. A matching information storage module storing corresponding distinctive identification information is attached to a bracelet for being worn on the infant's mother. The modules are readable by a compatible terminal only after a predetermined password is transmitted to them by the terminal.

Triggering elements attached to the clamp trigger an alarm system when the clamp and the infant it is attached to are carried from a protected area. A person wishing to carry the infant from the area is given permission to do so only after the identification information in her module is checked by hospital personnel for correspondence with the information in the infant's module.

Figure 1:
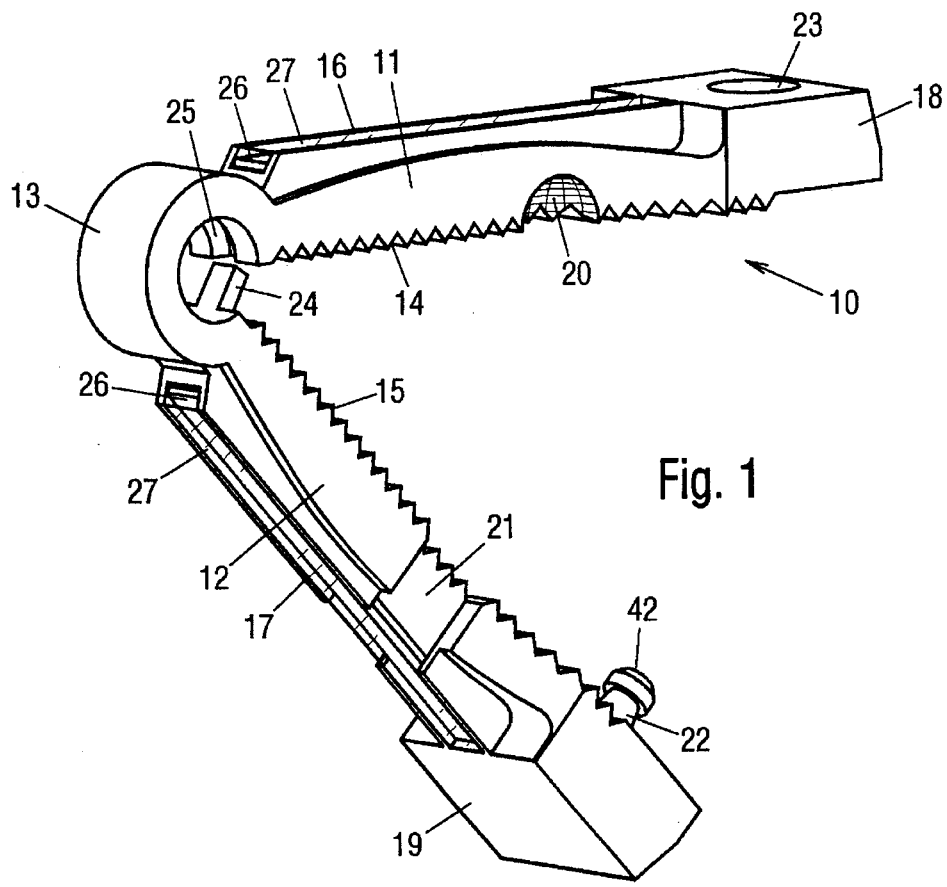
FIG. 1 is a side perspective view of an umbilical cord clamp in accordance with a preferred embodiment of the invention.

19, and a hole 23 is positioned on the outer side of grip portion 18. A resilient bar 24 is attached to the proximal end of arm 12, and a slot 25 is arranged on the inner side of loop-shaped hinge portion 13 adjacent the proximal end of arm 11. Bar 24 prevents an umbilical cord (not shown) from slipping into the opening of hinge portion 13. Elongated triggering elements 26 are positioned under transparent windows 27 in channels 16 and 17 for triggering a conventional alarm system (not shown) when they are carried past the alarm system's detection gate. A variety of materials can be used for triggering elements 26, such as the type of amorphous soft magnetic material sold under the trademark "SuperStrip" by Knogo of Hauppauge, New York.

DESCRIPTION—FIG. 2

Figure 2:
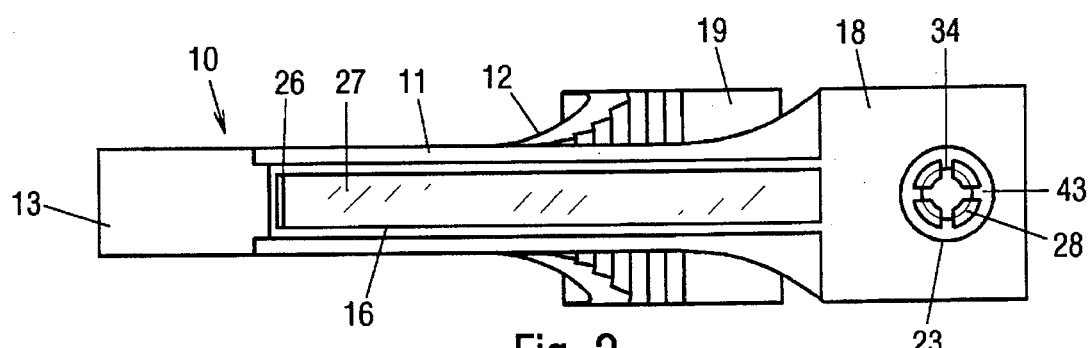
FIG. 2 is a top view of the umbilical cord clamp.

As shown in the top view of clamp 10 in FIG. 2, hole 23 extends partially into grip portion 18 from its outer side. A smaller hole 34 communicating with the inner end of hole 23 extends through to the inner side of grip portion 18, so that an annular shoulder 43 is formed between holes 34 and 23. Four spring flaps 28 are radially arranged around the perimeter of hole 34 on shoulder 43.

DESCRIPTION—FIGS. 3 AND 4

Figure 3:
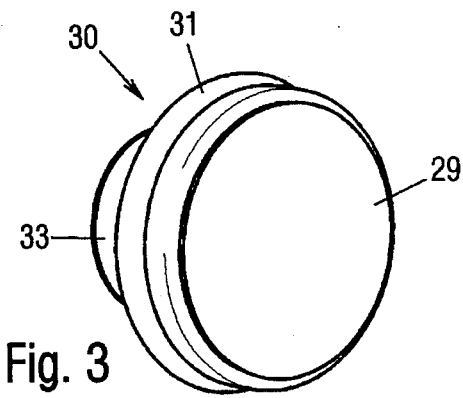
FIG. 3 is a side perspective view of an identification information storage module in accordance with a preferred embodiment of the invention.
Figure 4:
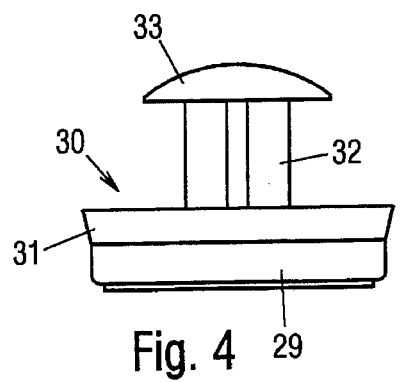
FIG. 4 is a top view of the identification information storage module.

As shown in the side perspective and top views in FIGS. 3 and 4, respectively, an identification information storage module 29 is attached to a mounting member 30, which includes a base 31, a stem 32, and a flange 33. Identification information storage module 29 is a reprogrammable, non-

| Drawing Reference Numerals | |
|---|---|
| 10. Umbilical Cord Clamp | 11. Arm |
| 12. Arm | 13. Loop-Shaped Hinge |
| 14. Knurls | 15. Knurls |
| 16. Channel | 17. Channel |
| 18. Cuip Portion | 19. Grip Portion |
| 20. Semi-Hemispherical Notch | 21. Constricted Neck Portion |
| 22. Projection | 23. Hole |
| 24. Bar | 25. Slot |
| 26. Triggering Elements | 27. Windows |
| 28. Spring Flaps | 29. Identification Information Storage Module |
| 30. Mounting Member | 31. Base |
| 32. Stem | 33. Flange |
| 34. Hole | 35. Wristband |
| 36. Identification Information Storage Module | 37. Base |
| 38. Terminal | 39. Display |
| 40. Keypad | 41. Touch Probe |
| 42. Enlarged Head | 43. Shoulder |

DESCRIPTION—FIG. 1

In accordance with a preferred embodiment of the invention shown in the side perspective view in FIG. 1, an infant identification and security apparatus includes an umbilical cord clamp 10 made of a flexible material, such as nylon. Clamp 10 includes a pair of arms 11 and 12 connected at an acute angle by a resilient, loop-shaped hinge portion 13 to form a "V" shape. Arms 11 and 12 include knurls 14 and 15, respectively, arranged on their inner sides, and channels 16 and 17, respectively, arranged on their outer sides. Arms 11 and 12 also include grip portions 18 and 19, respectively, arranged at their distal ends.

A semi-hemispherical notch 20 is arranged on one side and along an inner edge of arm 11. Arm 12 includes a constricted neck portion 21. A projection 22 with an enlarged head 42 is attached to the inner side of grip portion volatile digital memory module sold under the trademark "Touch Memory" by Dallas Semiconductor of Dallas, Tex. A conventional reader or terminal (not shown) is used to read information from and write information to module 29. The operation of module 29 and the terminal will be further explained in conjunction with FIG. 8.

DESCRIPTION—FIGS. 5 TO 7

Identification information storage module 29 and mounting member 30 are attached to umbilical cord clamp 10 by widening arms 11 and 12 to about 180 degrees, positioning stem 32 within loop-shaped hinge portion 13, and releasing the arms so that they return to their original positions.

Figure 5:
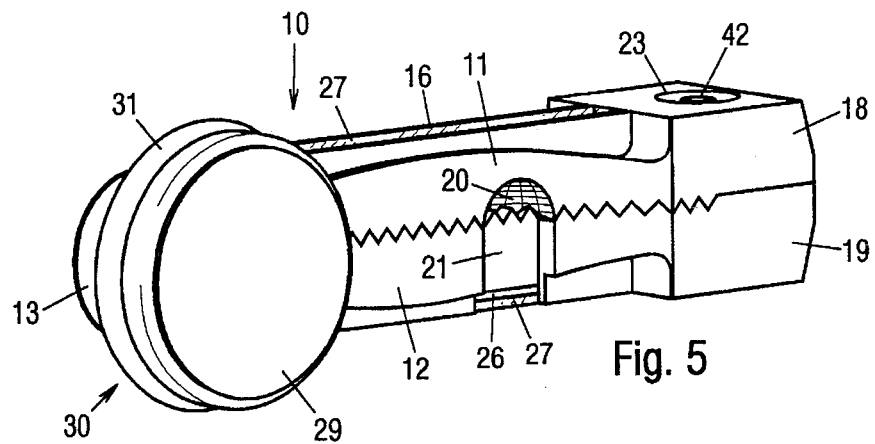
FIG. 5 is a side perspective view of the umbilical cord clamp and the identification information storage module assembled together.
Figure 6:
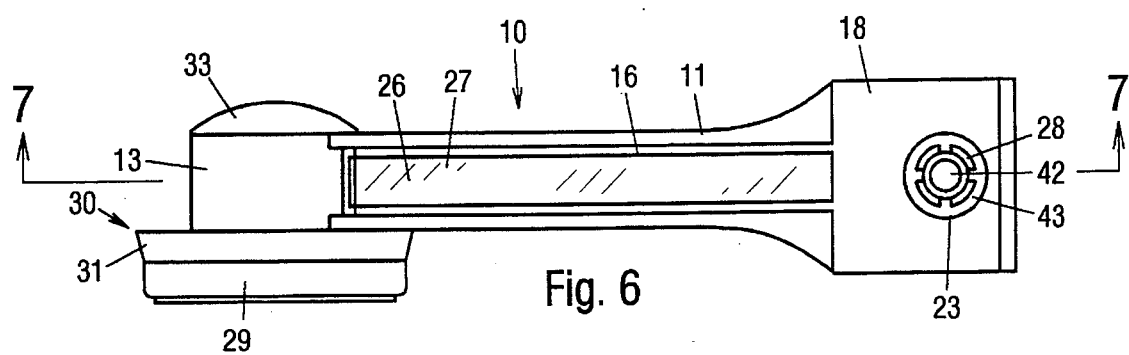
FIG. 6 is a top view of the umbilical cord clamp and the identification information storage module assembled together.
Figure 7:
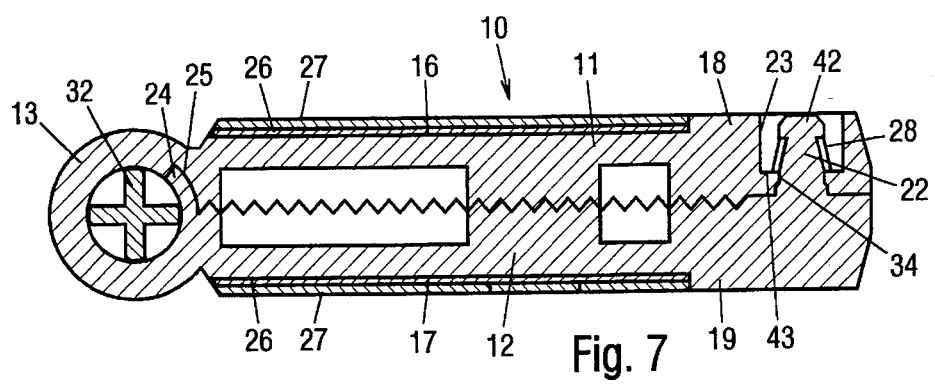
FIG. 7 is a sectional view of the umbilical cord clamp and the identification information storage module, taken along line 7—7 in FIG. 6.

To use, clamp 10 is positioned around an umbilical cord (not shown), and arms 11 and 12 are pressed together so that projection 22 is pushed through hole 34, until head 42 is snapped past spring flaps 28, as shown in FIGS. 5 to 7. The distal ends of inwardly-angled spring flaps 28 engage the lower rim of head 42 to lock arms 11 and 12 together. Spring flaps 28 are recessed deep within hole 23 to prevent tampering. Once locked in place, projection 22 cannot be pulled back out of hole 34. When clamp 10 is closed, resilient bar 24 is forced into conformity within curved slot 25.

If clamp 10 must be removed during a medical emergency, a conventional clamp cutting tool (not shown) can be used to cut arm 12 at constricted neck portion 21, where the arm is much thinner and easier to cut. Semi-hemispherical notch 20 provides clearance for the head of the clamp cutting tool.

DESCRIPTION—FIG. 8

Figure 8:
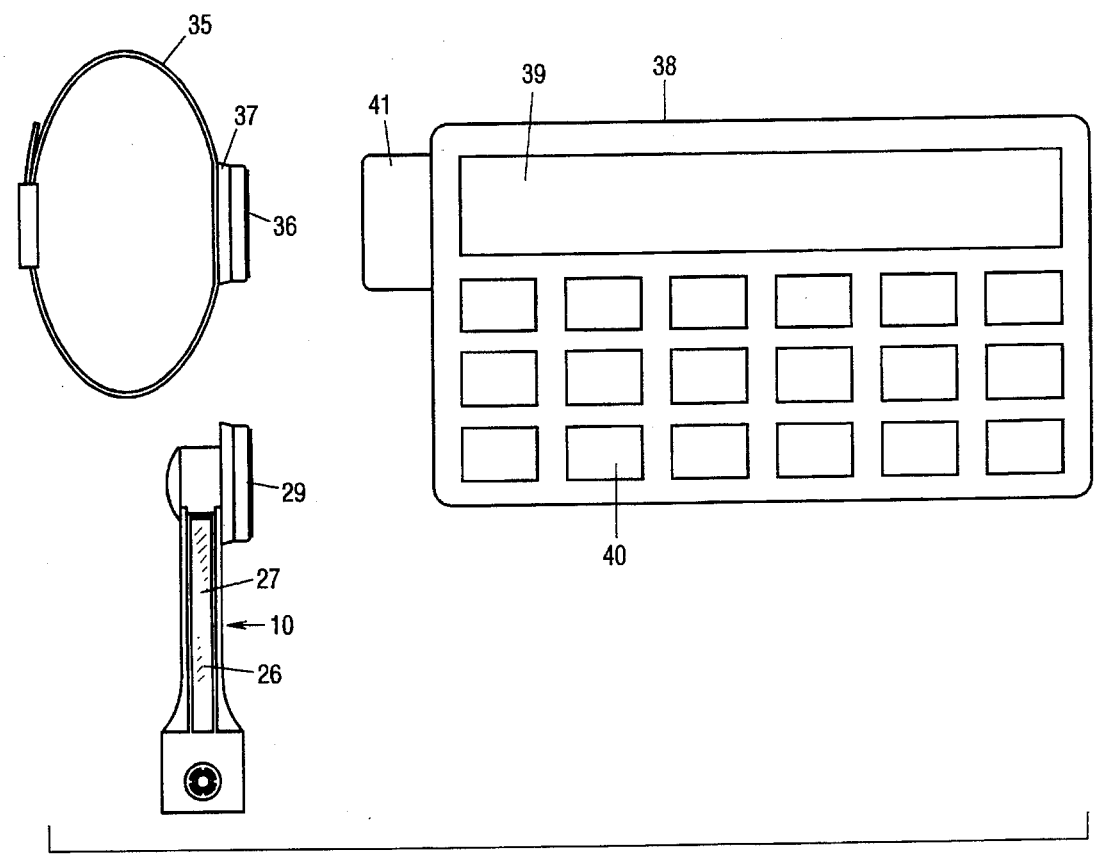
FIG. 8 shows the umbilical cord clamp and a bracelet in use with a terminal.

As shown in FIG. 8, clamp 10 is used in conjunction with a bracelet 35. Another identification information storage module 36 is mounted on a base 37 attached to bracelet 35. A conventional terminal 38 compatible with modules 29 and 36 is used to write and read distinctive identification information to and from the modules. Terminal 38 includes a display 39 for displaying information, a keypad 40 for entering information, and a touch probe 41 for mating with modules 29 and 36. The modules, which do not contain batteries, are supplied power momentarily by terminal 38 when they are in contact with touch probe 41 to transmit or receive information. A suitable terminal 38 is available as model "TI–74 S" from Texas Instruments of Dallas, Tex. Modules 29 and 36 include built-in password protection, so that a predetermined password must be entered via keypad 40 and transmitted to the modules before information can be read from or written to them. The password would be known only to authorized users of terminal 38, such as hospital personnel.

Clamp 10 and bracelet 35 are distributed as a matched set. Modules 29 and 36 on each set are preprogrammed with distinctive identification information, such as a matching serial number, at the factory. Additional distinctive identification information, such as a patient's name and other hospital records, can be programmed by hospital personnel into modules 29 and 36 by placing touch probe 41 thereon, entering the password on keypad 40, entering the identification information on keypad 40, and transmitting the information to the modules.

To use, bracelet 35 and clamp 10 from a matched set are attached to a mother and her infant, respectively. Permission to carry an infant from a maternity ward is only given to its mother. Before permission is granted to a person, the identification information on her bracelet is checked for correspondence with the identification information on the infant's clamp with the terminal, which confirms or refutes correspondence with predetermined audio tones. This procedure ensures that an infant is given only to its mother, and that infants will not be swapped by mistake. The identification information stored within modules 29 and 36 cannot be read by unaided eyes, i.e., a person without terminal 38, or a person without knowledge of the password, so that security is ensured.

Clamp 10 is also used in conjunction with a conventional alarm system (not shown) that includes a detection gate positioned at the entrance of a maternity ward, or any other suitable doorway. If an infant wearing clamp 10 is taken across the gate by an abductor, triggering elements 26 (one shown) will trigger the alarm to alert hospital personnel. The alarm can be deactivated temporarily when the infant is carried across the gate by an authorized person. Because triggering elements 26 are prominently visible on clamp 10 under windows 27 (one shown), they provide a powerful visual deterrent against abductions.

Conclusion, Ramifications, And Scope

Accordingly the reader will see that we have provided an infant identification and security apparatus that is provided with distinctive identification information not readable to an unaided eye, but that is only readable to authorized persons with a suitable terminal and the correct password. It can be programmed with a variety of patient identification information. It positively matches an infant to its mother to prevent abductions and inadvertent infant swapping. The clamp will trigger an alarm system if the infant to which it is attached is taken across a detection gate. The clamp cannot be easily removed from an infant by an unauthorized person to defeat the alarm system, but the clamp can be removed by hospital personnel with a clamp cutting tool in a medical emergency.

Although the above descriptions are specific, they should not be considered as limitations on the scope of the invention, but only as examples of the preferred embodiment. Many other ramifications and variations are possible within the teachings of the invention. For example, other types of identification information storage devices can be used, such as other types of digital memory chips or modules, scrambled optical patterns, etc. The identification information storage device can be preprogrammed with distinctive identification information in read-only memory. Instead of being preprogrammed at the factory, all the identification information can be programmed by a user with a terminal. Other suitable types of terminals or readers can be used. A terminal with read-only capability can be used, i.e., a terminal that cannot write information to an information storage module. Other types of triggering elements or devices can be used for triggering other types of alarm systems. Other than or in addition to the mother, the wristband can be worn on other persons authorized to remove the infant from the protected area. Instead of confirming or refuting correspondence with audio tones, the terminal can communicate with the user by displaying text messages. Therefore, the scope of the invention should not be determined by the examples given, but by the appended claims and their legal equivalents.

We claim:

1. An umbilical cord clamp, comprising:

first and second elongated arms each having a proximal end and a distal end, said arms being hingeably connected at said proximal ends forming a "V" shape for being positioned around an umbilical cord of an infant, each of said arms having a grip portion arranged at said distal end, each of said arms having an inner side and an outer side;

a first hole extending partially into said grip portion of said first arm from said inner side;

a second hole extending partially into said grip portion of said first arm from said outer side and communicating with said first hole, said second hole being coaxial with said first hole, said second hole having a larger diameter than said first hole, so that an annular shoulder is formed therebetween;

a plurality of outwardly extending spring flaps radially arranged around said shoulder; said spring flaps being recessed within said second hole; and a projection extending inwardly from said inner side of said grip portion of said second arm, said projection is arranged for being inserted into said first hole and positioned between said spring flaps when said arms are closed, said projection including an enlarged head portion at a distal end thereof, said enlarged portion being positioned outwardly of said spring flaps for preventing said projection from being withdrawn from said second hole when said arms are closed.

2. The umbilical cord clamp of claim 1, further including a flexible loop-shaped hinge portion connecting said arms at said proximal ends.

3. The umbilical cord clamp of claim 1, further including a plurality of knurls arranged on said inner sides of said arms for securely gripping said umbilical cord.

4. The umbilical cord clamp of claim 1, further including a constricted neck portion arranged on one of said arms, said neck portion being adapted to be cut by a cutting tool.

5. The umbilical cord clamp of claim 1, further including a channel arranged on an outer side of one of said arms, and triggering means disposed within said channel, said triggering means being adapted to trigger a compatible alarm system that generates an alarm when said triggering means is carried from a predetermined area.

6. The umbilical cord clamp of claim 1, further including a transparent window positioned over said triggering means.

7. An infant identification and security system, comprising:

umbilical cord clamping means; and identification information storage means attached to said umbilical cord clamping means and storing distinctive identification information therein, said distinctive identification information being adapted to be readable only by a compatible terminal, said distinctive identification information being unreadable to a person without said terminal.

8. The infant identification and security system of claim 7 wherein said identification information storage means comprises a non-volatile digital memory module.

9. The infant identification and security system of claim 8 wherein said non-volatile digital memory module is reprogrammable for changing said distinctive identification information.

10. The infant identification and security system of claim 7 wherein said identification information storage means includes password protection means for permitting access to said distinctive identification information stored therein only after a predetermined password is transmitted thereto by said terminal.

11. The infant identification and security system of claim 7, further including terminal means for reading said distinctive identification information in said identification information storage means.

12. The infant identification and security system of claim 7, further including triggering means attached to said umbilical cord clamping means and adapted to trigger a compatible alarm system that generates an alarm when said triggering means is carried from a predetermined area.

13. The infant identification and security system of claim 12 wherein said triggering means comprises an elongated triggering element disposed in an elongated channel on an outer side of said umbilical cord clamping means.

14. The infant identification and security system of claim 7, further including another identification information storage means containing corresponding distinctive identification information, said another identification information storage means being attached to a bracelet adapted to be worn on a person for identifying said person as being authorized to access said infant.

15. A method for identifying an infant and a person authorized to carry said infant from a predetermined area, and deterring unauthorized removal of said infant from said predetermined area, said predetermined area being equipped with an alarm system that generates an alarm when a triggering means is carried therefrom, comprising the steps of:

providing an umbilical cord clamp having identification information storage means attached thereto and storing distinctive identification information that is unreadable to unaided eyes, said umbilical cord clamp having triggering means attached thereto for triggering said alarm system when said triggering means is carried from said predetermined area;

clamping said umbilical cord clamp on an umbilical cord of an infant;

placing said infant within said predetermined area;

providing a wristband having another identification information storage means attached thereto and storing corresponding distinctive identification information that is unreadable to unaided eyes;

attaching said wristband on a wrist of a person authorized to carry said infant from said predetermined area;

providing terminal means for reading said distinctive identification information in said identification information storage means and said corresponding distinctive identification information in said another identification information storage means; and using said terminal to check for correspondence between said distinctive identification information in said identification information storage means on said umbilical cord clamp and said corresponding distinctive identification information in said another identification information storage means on said wristband attached to a person wishing to remove said infant from said predetermined area prior to authorizing removal.

16. The method of claim 15 wherein said distinctive identification information in said identification information storage means and said corresponding distinctive identification information in said another identification information storage means are readable only alter a predetermined password is entered into said terminal means.

* * * * *